United States Patent
Maschke

(10) Patent No.: US 8,382,372 B2
(45) Date of Patent: Feb. 26, 2013

(54) MEDICAL APPARATUS

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 118 days.

(21) Appl. No.: 12/499,145

(22) Filed: Jul. 8, 2009

(65) Prior Publication Data

US 2010/0008475 A1 Jan. 14, 2010

(30) Foreign Application Priority Data

Jul. 9, 2008 (DE) .......................... 10 2008 032 313

(51) Int. Cl.
*G01N 23/04* (2006.01)
*H05G 1/00* (2006.01)
*A61B 6/12* (2006.01)
*A61B 5/05* (2006.01)

(52) U.S. Cl. .......... 378/209; 378/63; 378/162; 378/205; 600/426

(58) Field of Classification Search ................ 378/4–20, 378/62, 63, 65, 162, 163, 204–206, 208, 378/209, 210; 600/425–429
See application file for complete search history.

(56) References Cited

U.S. PATENT DOCUMENTS

| | | | | |
|---|---|---|---|---|
| 6,402,762 B2 * | 6/2002 | Hunter et al. ................. | 606/130 |
| 6,416,219 B1 | 7/2002 | Pflaum et al. | |
| 6,618,612 B1 * | 9/2003 | Acker et al. ................. | 600/424 |
| 6,895,268 B1 * | 5/2005 | Rahn et al. ..................... | 600/429 |
| 6,907,629 B2 * | 6/2005 | Longton et al. .................. | 5/601 |
| 7,500,784 B2 * | 3/2009 | Grebner et al. ............... | 378/198 |
| 2003/0139670 A1 * | 7/2003 | Wist et al. ...................... | 600/426 |
| 2004/0073279 A1 * | 4/2004 | Malackowski et al. ......... | 607/88 |
| 2004/0199072 A1 * | 10/2004 | Sprouse et al. ............... | 600/424 |
| 2005/0065435 A1 * | 3/2005 | Rauch et al. ................... | 600/427 |
| 2005/0117710 A1 * | 6/2005 | Heinze et al. ................. | 378/197 |
| 2005/0152503 A1 * | 7/2005 | Rauh ............................. | 378/209 |
| 2005/0276383 A1 * | 12/2005 | Bertram et al. ............... | 378/181 |

(Continued)

FOREIGN PATENT DOCUMENTS

| DE | 19920008 B4 | 4/2004 |
|---|---|---|
| DE | 102005012700 A1 | 9/2006 |

(Continued)

OTHER PUBLICATIONS

Nagel et al., "Needle and catheter navigation using electromagnetic tracking for computer-assisted C-arm CT interventions"; Medical Imaging 2007: Visualization and Image-Guided Procedures. Edited by Kevin R. Cleary, Michael I. Miga; Proceedings of the SPIE, 2007; pp. 65090J (2007) • 1605-7422/07 vol. 6509.

*Primary Examiner* — Anastasia Midkiff

(57) ABSTRACT

The invention relates to a medical apparatus. The medical apparatus includes a patient support table with a patient support plate, a medical imaging device, a location and navigation facility integrated at least partially in the patient support table and/or the medical imaging device and a system controller, which is used to operate and/or control both the medical imaging device and also the location and navigation facility.

12 Claims, 2 Drawing Sheets

U.S. PATENT DOCUMENTS

| | | |
|---|---|---|
| 2006/0025668 A1 | 2/2006 | Peterson et al. |
| 2006/0285638 A1 | 12/2006 | Boese et al. |
| 2007/0030958 A1* | 2/2007 | Munger ............... 378/203 |
| 2007/0038064 A1* | 2/2007 | Creighton, IV ............ 600/407 |
| 2007/0197901 A1* | 8/2007 | Viswanathan ............ 600/411 |
| 2008/0221520 A1 | 9/2008 | Nagel et al. |
| 2008/0247506 A1 | 10/2008 | Maschke |
| 2008/0269602 A1* | 10/2008 | Csavoy et al. ............ 600/426 |
| 2008/0273659 A1* | 11/2008 | Guertin et al. ............ 378/65 |
| 2009/0168960 A1* | 7/2009 | Jongen et al. ............ 378/65 |
| 2009/0182248 A1* | 7/2009 | Jensen et al. ............ 600/595 |
| 2009/0182310 A1* | 7/2009 | Gertner et al. ............ 606/4 |

FOREIGN PATENT DOCUMENTS

| | | |
|---|---|---|
| DE | 102005028746 A1 | 12/2006 |
| DE | 102005044033 A1 | 3/2007 |
| DE | 102006036575 A1 | 2/2008 |
| DE | 102006061178 A1 | 6/2008 |
| WO | WO 2007029139 A2 | 3/2007 |

* cited by examiner

MEDICAL APPARATUS

CROSS REFERENCE TO RELATED APPLICATIONS

This application claims priority of German application No. 10 2008 032 313.6 filed Jul. 9, 2008, which is incorporated by reference herein in its entirety.

FIELD OF THE INVENTION

The invention relates to a medical apparatus, in particular for a minimally invasive intervention while navigating a medical object in the body of a patient.

BACKGROUND OF THE INVENTION

Minimally invasive medical interventions are being used increasingly. Thus in the treatment of coronary heart disease for example surgical bypass operations on the heart are increasingly giving way to balloon dilatation (PTCA=percutaneous transluminal coronary angioplasty) and stent insertion. Minimally invasive interventions are also being used increasingly in the field of biopsies, spinal therapies and tumor ablations.

During a minimally invasive intervention one or more medical instruments is/are inserted for example into the body of a patient for therapeutic or diagnostic purposes. Once a medical instrument has been inserted into the body of the patient, it is no longer directly visible to a physician carrying out the intervention. To navigate the instrument in the body of the patient it must therefore be visualized appropriately for the physician in image information. Many different types of systems and methods are currently available to determine the position of the instrument in the body of the patient during minimally invasive medical interventions, as required to visualize the instrument, in particular the tip of the instrument, in image information from inside the body of the patient.

Progress in 3D x-ray imaging in the meantime allows 3D mapping of organs and also instruments in the body of a living being. However it is still difficult to distinguish between instruments, organs and bones in the x-ray image, while at the same time using as little x-ray radiation as possible for imaging and to determine instrument position.

In this context a method for determining the position and orientation of an object, in particular a catheter, in a patient based on two-dimensional x-ray images using so-called template matching is described in DE 10 2005 028 746 A1. A three-dimensional template of the catheter is produced here based on the known structural properties of the catheter. To determine the position and orientation of the catheter in the body of a living being the three-dimensional template is projected onto a two-dimensional plane and the projection image produced is compared with an x-ray image, in which the catheter is mapped. Parameters determined initially for the position and orientation of the template in space are then modified iteratively and a degree of similarity is determined, which is used to determine the position and orientation of the catheter.

An electromagnetic navigation system AURORA from the company NDI, Waterloo, Ontario, Canada is described in "Needle and catheter navigation using electromagnetic tracking for computer-assisted C-arm CT interventions", Markus Nagel, Martin Hoheisel, Ralf Petzold, Willi A. Kalender and Ulrich H. W. Krause, Medical Imaging 2007: Visualization and Image-Guided Procedures, edited by Kevin R. Cleary, Michael I. Miga, Proc. of SPIE Volume 6509, 65090J, (2007) 1605-7422/07/$18 doi: 10.1117/12.709435. The electromagnetic navigation system comprises a field generator for generating an electromagnetic field, to determine positions and orientations of medical instruments, each having small induction coils at their tip. The AURORA system can use the induced voltages to determine the position and orientation of the respective instrument.

To improve the accuracy of instrument location and to improve the determination of the coordinate transformations between an image coordinate system and a coordinate system assigned to the navigation system, also referred to as registration, navigation systems based on x-ray radiation and/or on electromagnetic waves frequently have a plate comprising x-ray markers and/or electromagnetic markers, which is disposed below a patient, on whom the minimally invasive intervention is carried out. Thus the system described in "Needle and catheter navigation using electromagnetic tracking for computer-assisted C-arm CT interventions", Markus Nagel, Martin Hoheisel, Ralf Petzold, Willi A. Kalender and Ulrich H. W. Krause, Medical Imaging 2007: Visualization and Image-Guided Procedures, edited by Kevin R. Cleary, Michael I. Miga, Proc. of SPIE Volume 6509, 65090J, (2007) 1605-7422/07/$18 doi: 10.1117/12.709435 has a so-called registration panel with five x-ray markers, which can be detected automatically in x-ray images, and with an electromagnetic sensor, which can be detected using the AURORA system. The registration panel is not only used for registration here but also as a reference system during the navigation of instruments.

One disadvantage of this solution is that the plate registration panel comprising the x-ray markers and the electromagnetic marker or is uncomfortable for the patient and can cause the patient to suffer bruises or pressure sores during longer interventions.

The field generator of the electromagnetic navigation system must also be secured to a patient support apparatus holding the patient or be disposed on a separately embodied stand adjacent to the patient support apparatus, in order to provide the electromagnetic field for navigation in the desired spatial region. However this structure hinders access to the patient and also increases the risk of collision, for example with a medical imaging device used for interoperative imaging during the intervention.

The electromagnetic navigation system also has a PC (personal computer) with a display apparatus on a cart or rack to operate the electromagnetic navigation system. The cart or rack also takes up space around the patient support apparatus.

Also patient administration and the documentation of navigation-assisted interventions including the recording of consumables used during such a medical intervention is not integrated due to the different items of equipment and individual components used, which is disadvantageous for the most optimal medical workflow possible, as data relating to a medical intervention, e.g. patient data, must be managed, input, modified, transferred to a patient file, etc. both at the electromagnetic navigation system and also at the imaging device used.

SUMMARY OF THE INVENTION

The object underlying the invention is therefore to specify an apparatus of the type mentioned in the introduction, in such a manner that the preconditions for workflow improvement are created during a medical intervention using the apparatus.

According to the invention this object is achieved by a medical apparatus having a patient support table with a patient support plate, a medical imaging device, a location and navigation facility integrated at least partially in the patient support table and/or the medical imaging device and a system controller, which is used to operate and/or control both the medical imaging device and the location and navigation facility. It is therefore proposed firstly to provide a system controller for a medical apparatus, in particular for minimally invasive interventions, which has a patient support table, a medical imaging device and a location and navigation facility. The controller of the medical imaging device preferably assumes the function of system controller. There is then no need for a separately embodied controller in the form of a computer or PC (personal computer) in particular for the location and navigation facility, thereby keeping space free around the supported patient. The location and navigation facility is also at least partially, preferably wholly, integrated in the patient support table and/or in the medical imaging device, which means that components of the location and navigation facility, e.g. a field generator, field coils, sensors or markers in the case of an electromagnetic location and navigation facility, are integrated in the sense of being accommodated in the patient support table and/or in the medical imaging device and therefore do not take up separate space. These measures create the preconditions for the work sequence or workflow during a medical, in particular during a minimally invasive, intervention on a patient using the medical apparatus to be improved, as not only is free space created around the patient support table but also the entire patient administration process for the medical intervention, i.e. for example calling up or retrieving patient and image data from a HIS (Hospital Information System), inputting, modifying and storing data in an electronic patient file in the HIS and recording consumables used for the intervention, can only be implemented by way of the system controller.

In one variant of the invention the system controller or an image system comprising the medical imaging device and image processing units includes and can run both the operating software for the medical imaging device and also the operating software for the location and navigation facility.

According to one variant of the invention the medical imaging device of the medical apparatus is an x-ray device. The x-ray device is preferably a C-arm x-ray device. The C-arm having an x-ray radiation source and an x-ray radiation receiver can be disposed here on a buckling arm robot, as described in DE 10 2005 012 700 A1.

According to one embodiment of the invention the location and navigation facility of the medical apparatus is an electromagnetic location and navigation facility, which preferably has a field generator for generating a variable electromagnetic field and coils that are disposed or can be disposed at the tip or distal end of minimally invasive medical instruments to determine the position of the instruments. The medical instruments can be catheters, biopsy needles, ablation needles, stents, endoscopes etc.

According to a further variant of the invention the operating software of the location and navigation facility is integrated as a software module or plug-in in the operating software of the medical imaging device. The operating software of the location and navigation facility can preferably be called up and/or operated by way of a menu in the operating software of the medical imaging device. The input means in the form of a keyboard, computer mouse, etc. of the system controller or medical imaging device are preferably also used to input data into and/or control the location and navigation facility.

In one embodiment of the invention the medical apparatus has a monitor, a group of monitors or a large screen, it being possible to display menus, data and/or image data of the medical imaging device and/or the location and navigation facility on at least one monitor or a display field of the large screen, which can be divided into display fields.

According to a further embodiment of the invention the medical apparatus has a DICOM interface (Digital Imaging and Communications in Medicine) for patient and image data connected to the system controller for patient administration purposes. According to one variant of the invention an intervention carried out on a patient using the location and navigation facility can be documented with the aid of the operating software of the location and navigation facility and can be fed to an electronic patient file of the patient by way of the DICOM interface.

At least one x-ray positive and/or at least one electromagnetic marker or sensor of the electromagnetic location and navigation facility is integrated in a fixed or movable manner in the patient support plate, i.e. accommodated therein, which cannot generally be seen directly from the outside, if corresponding visual markings are not present. This makes it possible to dispense with a marker plate or the registration panel described in the introduction.

According to one variant of the invention the field generator of the electromagnetic location and navigation facility is an integral part of the patient support table. The field generator here can be disposed in or below the patient support plate in a fixed or movable manner relative to the patient support plate. In the case of a movable arrangement in particular rails or a rail system for example can be provided to displace the field generator transversely and longitudinally relative to the patient support plate.

According to one embodiment of the invention the field generator is disposed in a fixed or movable drawer of the patient support plate, like an x-ray cassette in a bucky table, said drawer being disposed in or below the patient support plate and being able to be moved or displaced to a desired position relative to the patient support plate or a patient.

Alternatively the field generator can be disposed on a retaining apparatus of the patient support plate that is fixed or movable in relation to the patient support plate and is used to fold the field generator out and in relative to the patient support plate. The retaining apparatus can be displaced transversely or longitudinally relative to the patient support plate again by means of rails. The retaining apparatus can be configured as an articulated arm, a swan neck, etc.

A further alternative is to integrate the field generator of the electromagnetic location and navigation facility in the medical imaging device. The field generator can thus be integrated in the x-ray device. To prevent imaging with the x-ray device being negatively influenced by the field generator, which generates a variable electromagnetic field, in particular when the field generator is disposed in proximity to the x-ray radiation source or the x-ray radiation receiver, according to one variant of the invention field shields are provided for the x-ray radiation source and/or the x-ray radiation receiver. The x-ray radiation receiver is also advantageously embodied as an aSi flat panel detector here.

According to a further variant of the invention the field generator of the electromagnetic location and navigation facility can be attached to a buckling arm robot disposed on the patient support table for positioning relative to a patient.

According to a further alternative embodiment of the invention the electromagnetic location and navigation facility has a number of field coils to generate different electromagnetic fields, these being disposed in a distributed manner at different points in or on the patient support plate.

The medical apparatus preferably also has a collision detector unit interacting with the system controller, to prevent collisions for example of the medical imaging device and the buckling arm robot for guiding the field generator.

The medical apparatus is provided in particular for use for a biopsy, a tumor ablation or for diagnostic or therapeutic interventions on the lungs or heart of a patient.

BRIEF DESCRIPTION OF THE DRAWINGS

Exemplary embodiments of the invention are illustrated in the accompanying schematic drawings, in which.

DETAILED DESCRIPTION OF THE INVENTION

Figure 1:
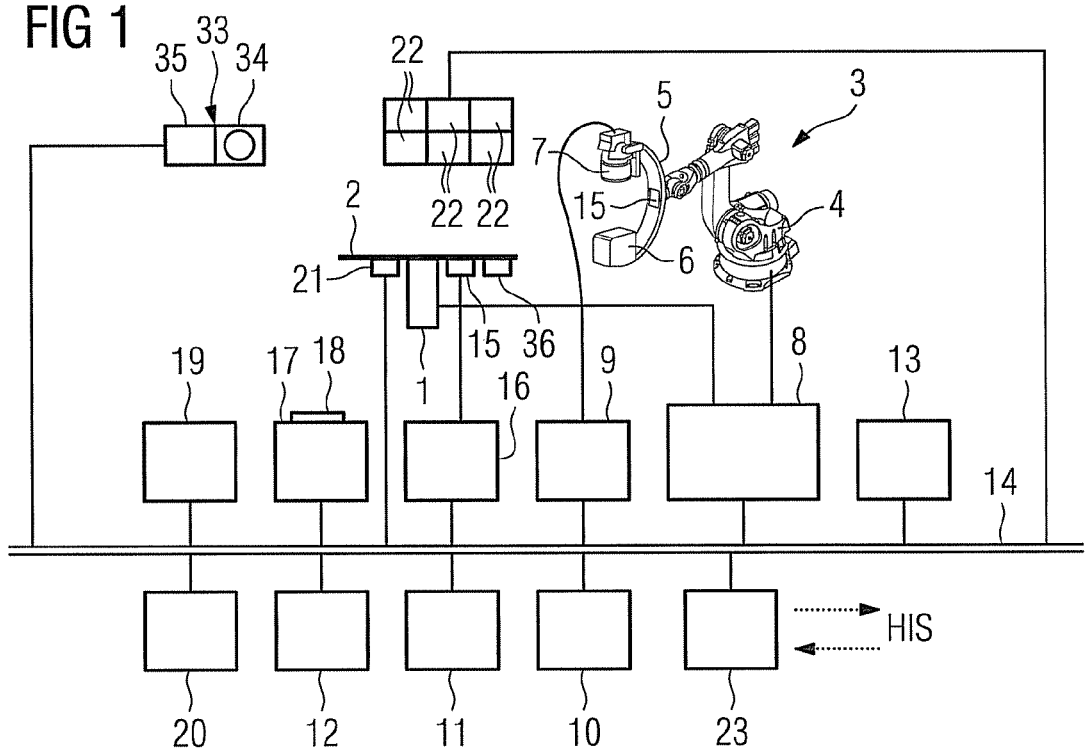
FIG. 1 shows a medical apparatus.

FIG. 1 shows the medical apparatus for carrying out a medical intervention, in particular a minimally invasive medical intervention on a patient (not shown explicitly). The intervention can be for example a biopsy, a catheter navigation, a tumor ablation or generally diagnostic or therapeutic interventions on the heart or lungs of a patient.

The apparatus comprises a patient support table 1 with a patient support plate 2, a medical imaging device in the form of a C-arm x-ray device 3 and in the present exemplary embodiment an electromagnetic location and navigation facility.

As described in DE 10 2005 012 700 A1 the C-arm x-ray device 3 has a buckling arm robot 4, which guides a C-arm 5, on which an x-ray radiation source 6 and an x-ray radiation receiver 7 are disposed opposite one another. In the present exemplary embodiment the x-ray radiation receiver 7 is an x-ray image amplifier. However the x-ray radiation receiver 7 can also be embodied as an aSi flat panel detector.

The C-arm x-ray device 3 has a controller 8, which in the present exemplary embodiment has the function of a system controller 8 of the medical apparatus. Also assigned to the C-arm x-ray device 3 are a computation unit 9 for preprocessing x-ray images, a computation unit 10 for calibration or registration with the electromagnetic location and navigation facility, a computation unit 11 for image correction and a computation unit 12 for image reconstruction, for image processing for x-ray images including soft tissue in particular and for image merging, image segmentation and automatic image segmentation. An image storage unit 13 is also present, being connected, like the computation units 8 to 12, to a data bus 14.

It is possible with the C-arm x-ray device 3 and optionally the assigned computation units to record and display 2D x-ray projections or fluoroscopy images from different projection directions of a patient supported on the patient support table 1 in the manner known per se. It is also possible with the C-arm x-ray device 3 to reconstruct and display 3D images of the inside of the body of a patient from 2D x-ray projections recorded from different projection directions.

The electromagnetic location and navigation facility is controlled by the system controller 8 and therefore does not have its own controller. In the present exemplary embodiment shown in FIG. 1 the electromagnetic location and navigation facility comprises a field generator 15 for generating a variable electromagnetic field, electromagnetic sensors or coils (not shown explicitly) disposed in a defined manner at or on the tips or distal ends of medical intervention instruments, such as biopsy needles, catheters etc., an actuation unit 16 for the field generator 15, a computation unit 17 for preprocessing the signals originating from the electromagnetic sensors or coils of the intervention instrument(s) with a signal interface 18 for the signals and a computation unit 19 for image processing based on the signals of the electromagnetic sensors or coils. The actuation unit 16, the preprocessing unit 17 and the computation unit 19 for image processing are likewise connected to the data bus 14. The coils or sensors having coils disposed in the intervention instruments (not shown) are connected by way of cables or by radio to the signal interface 18 of the computation unit 17 for preprocessing the signals. Provision can however also be made for a connector interface 36 for coils or electromagnetic sensors having coils, which are disposed in or on a medical instrument, on the patient support table 1. The interface 36 is connected in a manner not shown to the signal interface 18.

When the medical apparatus is in use, the electromagnetic field of the field generator 15 induces voltages in the small coils of the intervention instruments, which are measured using the computation unit 17 for preprocessing and then preferably used to determine the position and orientation of the tip of the respective intervention instrument in a coordinate system assigned to the location and navigation facility. However the computation unit 19 can also be used to generate images based on the signals in the manner of a mapping system.

The patient support table 1 can also be a patient support table, as described for example in DE 199 20 008 B4. In the present exemplary embodiment the patient support table 1 and/or the patient support plate 2 is/are set and/or moved using the system controller 8.

The system controller 8 not only includes the operating software for the C-arm x-ray device 3 and actuates the computation units 9 to 12 assigned to the C-arm x-ray device 3, it also includes the operating software of the patient support table 1 and in particular the operating software of the electromagnetic location and navigation apparatus and actuates the computation units 16, 17 and 19 assigned to the electromagnetic location and navigation apparatus. The operating software of the electromagnetic location and navigation apparatus is integrated as a software module or plug-in in the operating software of the C-arm x-ray device 3. The operating software of the electromagnetic location and navigation apparatus can be selected, called up and operated by way of a menu in the operating software of the C-arm x-ray device 3. In particular it is possible to call up and operate a function card for the electromagnetic location and navigation apparatus by way of a menu in the operating software of the C-arm x-ray device 3.

Similarly the operating software for the patient support table 1 is also integrated in the operating software of the C-arm x-ray device 3, so that this can also be selected, called up and operated by way of a menu in the operating software of the C-arm x-ray device 3.

The medical apparatus can be operated by way of the operating facilities and/or input means (not explicitly shown) of the C-arm x-ray device 3. The operating facilities and/or input means here can include a keyboard, computer mouse, trackball, touch screen etc. in the manner known per se. The medical apparatus also has operating facilities 20 and/or input means 20 connected to the data bus 15 as well as operating facilities 21 and/or input means 21 in proximity to the patient connected to the data bus 15 and disposed on or in the region of the patient support table 1, which can likewise include a keyboard, computer mouse, trackball, touch screen etc.

In the present exemplary embodiment menus of the operating software, data in general, patient data, image information etc. obtained using the C-arm x-ray device 3 or the electromagnetic location and navigation apparatus, etc. are displayed on a group of six monitors 22. A first monitor 22 here can be provided as the display apparatus for the electromagnetic location and navigation apparatus, a second monitor 22 as the display apparatus for the C-arm x-ray device 3, a third monitor 22 as the display apparatus for the patient support table, a fourth monitor 22 as the display apparatus for x-ray images, overlaid images, etc.

Alternatively instead of the group of monitors 22 a large screen can also be used, which is or can be divided into different display fields for corresponding displays of data and images from the different items of equipment.

A DICOM interface 23 for patient and image data is provided for patient administration. This allows the system controller 8 to call up patient and image data from an electronic patient file in a HIS (Hospital Information System). Likewise data relating to a medical intervention, be it image data, patient data, diagnostic or therapeutic data, findings, protocols, data relating to consumables, etc. can be fed with the aid of the DICOM interface 23 for example using DICOM-MPPS (Modality Performed Procedure Step) to a hospital network, an electronic patient file in a HIS or a billing system.

Figure 2:
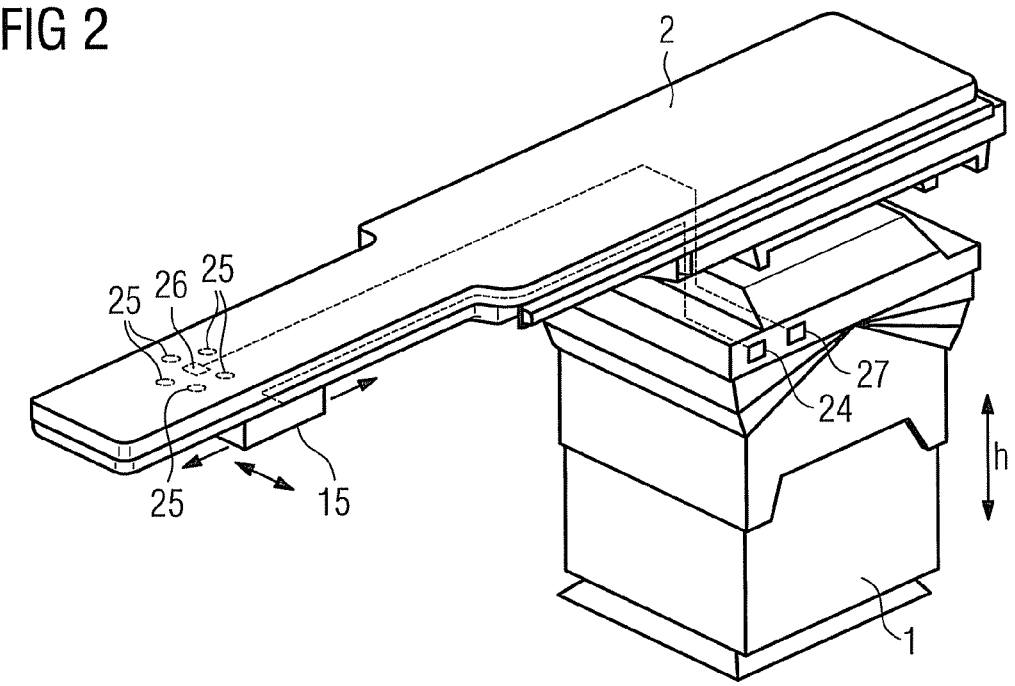
FIG. 2 shows a patient support table of the medical apparatus with a movable field generator, integrated x-ray markers and an integrated electromagnetic marker.

The field generator 15 of the electromagnetic location and navigation apparatus is disposed on the patient support plate 2, as shown in FIG. 1. The field generator 15 here can be disposed below the patient support plate 2 in such a manner that it can be displaced and/or moved transversely and/or longitudinally relative to the patient support plate 2, as shown in FIG. 2. Rails (not shown) can for example be provided for this purpose, on which the field generator is disposed in a displaceable manner. The electrical contacting of the field generator 15 is effected by way of a connector 24.

In the present exemplary embodiment a number of x-ray positive markers 25 and an electromagnetic marker 26 of the electromagnetic location and navigation apparatus having six degrees of freedom are also integrated in a defined manner in the patient support plate 2, so there is no need for the marker plate and/or registration panel mentioned in the introduction. The electromagnetic marker 26 can be contacted by way of an electrical connector 27.

The x-ray positive markers 25 and the electromagnetic marker 26 are also used, like the marker plate and/or registration panel mentioned in the introduction for example to register the C-arm x-ray device 3 and the electromagnetic location and navigation facility with one another, during which a coordinate transformation is determined between a patient or image coordinate system and a coordinate system assigned to the electromagnetic location and navigation facility. Only then is it possible to overlay an image of at least one tip of an intervention instrument in an image of the inside of the body of a patient obtained using the C-arm x-ray device 3 in the correct position and with the correct alignment.

The five x-ray positive markers 25 are preferably spherical and made of lead. The markers 25 have a diameter of approximately 3 to 15 mm and can be seen clearly in x-ray images. In the present exemplary embodiment the electromagnetic marker 26 or sensor 26 has six receiver coils (not explicitly shown), which are spatially aligned in a different manner relative to one another, in other words it has six degrees of freedom. The markers 25 and the marker 26 are disposed in a defined manner relative to one another.

Figure 3:
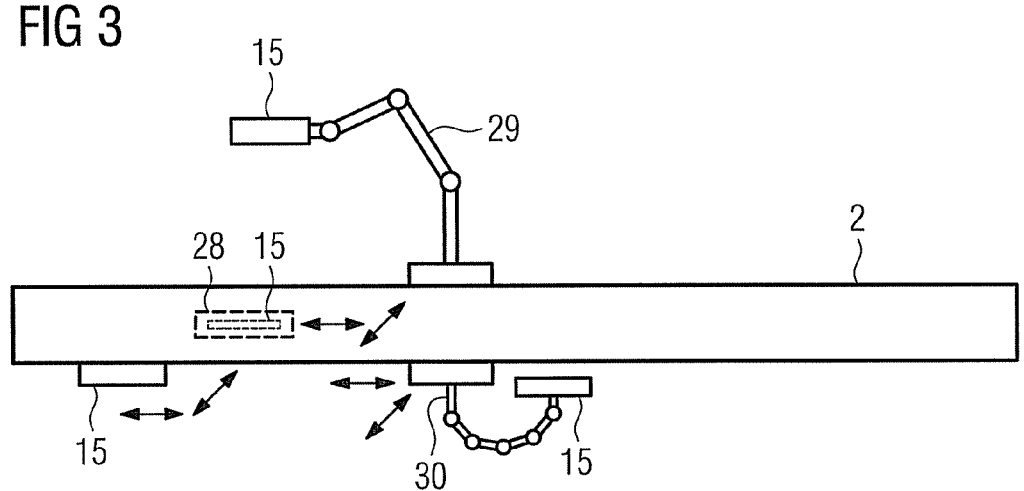
FIG. 3 shows a side view of a patient support plate of the medical apparatus with alternative arrangements for the field generator and FIG. 4 shows a patient support table of the medical apparatus with integrated field coils, x-ray markers and an electromagnetic marker.

Further alternative arrangements of the field generator 15 in or on the patient support plate 2 are shown in FIG. 3. According to a first alternative the field generator 15 can be disposed in a fixed or movable drawer 28. The drawer 28 here is preferably integrated in the patient support plate 2. Despite integration the drawer 28 can however be moved into a position, in which the field generator 15 is accessible from outside.

According to a second alternative the field generator 15 can be disposed on a buckling arm robot 29 secured to or on the patient support plate 2. The buckling arm robot 29 can be used to move the field generator 15 into different positions relative to a patient positioned on the patient support plate 2. The buckling arm robot 29 can be actuated by the system controller 8 in this process.

According to a third alternative the field generator 15 can be disposed on a retaining apparatus 30 of the patient support plate 2, which is fixed or can be moved transversely and/or longitudinally relative to the patient support plate 2. The retaining apparatus 30 can be folded out and in. The field generator can thus be moved as required by folding the retaining apparatus 30 out into a desired position relative to a patient. Otherwise the retaining apparatus 30 is folded in with the field generator, so that the field generator is positioned in a park position below the patient support plate 2.

According to a fourth alternative the field generator can be integrated in the C-arm x-ray device 3, for example in the C-arm 5. In such an instance, in contrast to the magnetic tracking system described in WO 2007/029139 A2, with which field generators are disposed on an x-ray radiation source and an x-ray radiation detector, field shields are provided, for example in the form of metallic plates, for the x-ray radiation source 6 and the x-ray image amplifier 7, to prevent the electromagnetic field of the field generator having a negative influence on the image quality of the images produced using the C-arm x-ray device 3. As mentioned above, it is possible with this embodiment of the invention to use an aSi flat panel detector as the x-ray radiation receiver.

Regardless of the arrangement alternative selected for the field generator 15, an electrical connector is always assigned to the field generator 15, so that the field generator 15 can be connected to its actuation unit 16.

Figure 4:
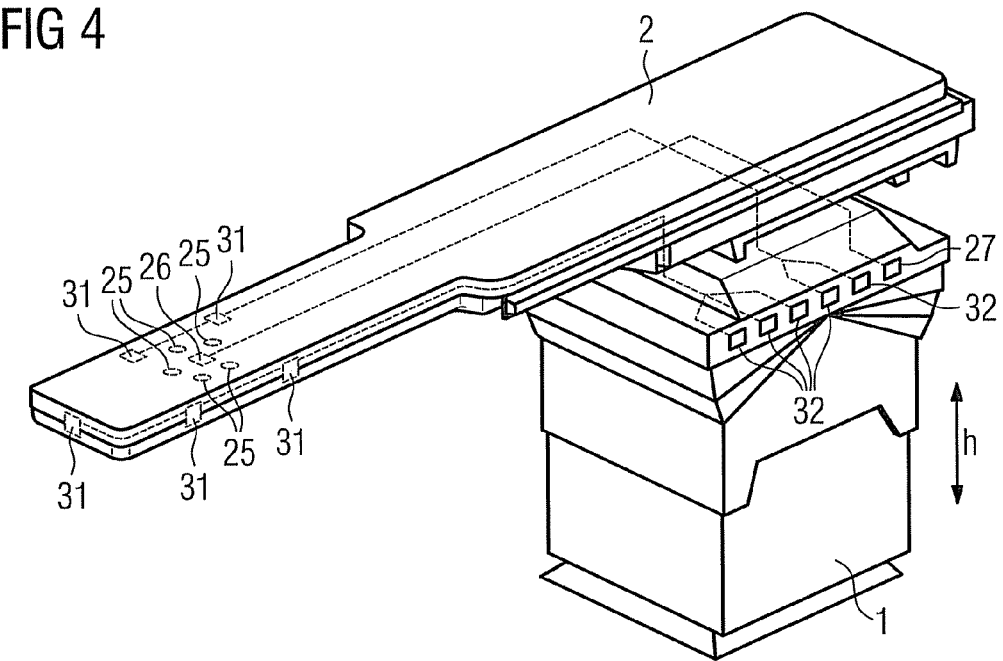

One alternative to using a field generator is to use a number of field coils 31 to generate different electromagnetic fields. FIG. 4 shows the use of such field coils 31. According to the exemplary embodiment shown in FIG. 4 five field coils 31 are integrated in the patient support plate 2 and can be contacted by means of connectors 32 in this instance to the actuation unit 16 for the field coils 31.

In the present exemplary embodiment the medical apparatus also has a collision detector unit 33. The collision detector unit 33 can have a camera 34 for example and a computer 35 to evaluate the camera images, these being able to monitor the space around the patient support table 1 for collisions. This is primarily of benefit when the field generator 15 is disposed for example on the buckling arm robot 29, so that collisions with the C-arm x-ray device 3 in particular would be possible. Based on the data from the collision detector unit 33 and the control data it has itself relating to the patient support table 1, the C-arm x-ray device 3 and the buckling arm robot 29, the system controller 8 therefore knows the positions of the patient support table 1, the C-arm x-ray device 3 and the buckling arm robot 29, so that collisions between the various items of equipment can be avoided.

The medical imaging device described does not necessarily have to be an x-ray device and/or a C-arm x-ray device. The medical imaging device can also be an x-ray computed tomograph or an ultrasound device.

The control computer 8 also does not necessarily have to be the control computer of the medical imaging device. Instead the control computer can also be a separately embodied computer or a computation unit.

From a functional point of view the electromagnetic location and navigation facility can be the AURORA tracking System from Northern Digital Inc., Waterloo, Ontario, Canada for example, as described for example in "Needle and catheter navigation using electromagnetic tracking for computer-assisted C-arm CT interventions", Markus Nagel, Martin Hoheisel, Ralf Petzold, Willi A. Kalender and Ulrich H. W. Krause, Medical Imaging 2007: Visualization and Image-Guided Procedures, edited by Kevin R. Cleary, Michael I. Miga, Proc. of SPIE Volume 6509, 65090J, (2007) 1605-7422/07/$18*doi: 10.1117/12.709435.

With the present invention, depending on the embodiment, the electromagnetic location and navigation facility is integrated partially, preferably wholly, in the patient support table and/or the medical imaging device, thereby allowing an improved work sequence and/or workflow to be achieved.

The invention claimed is:

1. A medical apparatus, comprising:
   a patient support table with a patient support plate;
   a marker arrangement integrated in the patient support plate, wherein the marker arrangement comprises at least one of an x-ray marker and an electromagnetic marker, the marker arrangement in the patient support plate effective to dispense with a marker plate or registration panel in contact with a portion of the body of a patient;
   a medical imaging device;
   a location and navigation device to determine position and orientation of a tip of an intervention instrument inside the patient, the location and navigation device integrated in the patient support table, wherein the location and navigation device comprises a field generator;
   structure arranged to provide slidable movement of the field generator relative to the patient support table, wherein the structure arranged to provide the slidable movement to the field generator relative to the patient support table is a rail system affixed to the patient support plate, wherein the rail system comprises rails arranged to provide respective transverse and longitudinal movements to the field generator relative to the patient support plate; and
   a system controller that operates and controls the medical imaging device and the location and navigation device.

2. The medical apparatus as claimed in claim 1, wherein the system controller is a controller of the medical imaging device.

3. The medical apparatus as claimed in claim 1,
   wherein the system controller comprises an operating software for the medical image device and an operating software for the location and navigation device,
   wherein the operating software for the location and navigation device is integrated as a software module or plug-in in the operating software for the medical imaging device, and
   wherein the operating software for the location and navigation device is operated by a menu in the operating software for the medical imaging device.

4. The medical apparatus as claimed in claim 1, wherein the medical imaging device comprises an input unit that inputs data into the location and navigation device or controls the location and navigation device.

5. The medical apparatus as claimed in claim 1, further comprising a monitor to display menus, or image data of the medical imaging device, or data of the location and navigation device.

6. The medical apparatus as claimed in claim 1,
   wherein the system controller is connected to a Digital Imaging and Communications in Medicine interface for patient administration, and
   wherein an intervention carried out on a patient using the location and navigation device is documented and fed to an electronic patient file of the patient by the interface.

7. The medical apparatus as claimed in claim 1,
   wherein the location and navigation device comprises a plurality of field coils to generate different electromagnetic fields, and
   wherein the field coils are disposed at different points in or on the patient support plate.

8. The medical apparatus as claimed in claim 1, further comprising a collision detector unit that interacts with the system controller.

9. The medical apparatus as claimed in claim 1, wherein the medical apparatus is used for a biopsy, or a tumor ablation, or a diagnostic intervention, or a therapeutic intervention on lungs or heart of a patient.

10. The medical apparatus as claimed in claim 1, wherein the location and navigation device is an electromagnetic location and navigation device.

11. The medical apparatus as claimed in claim 1,
    wherein the medical imaging device is an x-ray device comprising an x-ray radiation source and an x-ray radiation receiver,
    wherein the medical imaging device comprises field shields for the x-ray radiation source or the x-ray radiation receiver, and
    wherein the x-ray radiation receiver is an aSi flat panel detector.

12. A medical apparatus, comprising:
    a patient support table with a patient support plate;
    a marker arrangement integrated in the patient support plate, wherein the marker arrangement comprises at least one of an x-ray marker and an electromagnetic marker, the marker arrangement in the patient support plate effective to dispense with a marker plate or registration panel in contact with a portion of the body of a patient;
    a medical imaging device;
    a location and navigation device to determine position and orientation of a tip of an intervention instrument inside the patient, the location and navigation device comprising a field generator attached to a buckling arm robot mechanically connected to the patient support table; and
    a system controller that operates and controls the medical imaging device and the location and navigation device.

* * * * *